United States Patent [19]

Arashiba et al.

[11] Patent Number: 4,994,586
[45] Date of Patent: Feb. 19, 1991

[54] METHOD FOR PREPARING EPOXY COMPOUND

[75] Inventors: Nobumasa Arashiba, Yokohama; Takashi Shimizu, Osaka; Masaru Takeshita, Osaka; Akira Otsu, Osaka, all of Japan

[73] Assignee: Mitsui Toatsu Chemicals, Incorporated, Chiyoda, Japan

[21] Appl. No.: 357,201

[22] Filed: May 25, 1989

[30] Foreign Application Priority Data

May 26, 1988 [JP] Japan .................................. 63-126912

[51] Int. Cl.$^5$ .......................................... C07D 301/19
[52] U.S. Cl. .................................................... 549/529
[58] Field of Search .......................................... 549/529

[56] References Cited

U.S. PATENT DOCUMENTS 3,526,645  9/1970  Vangermain et al. ............. 549/529
3,947,500  3/1976  Kollar .............................. 549/529

FOREIGN PATENT DOCUMENTS 1460575  12/1966  France .
133279   10/1981  Japan .
100561   3/1979   Poland .
1112887  5/1968   United Kingdom .
1115220  5/1968   United Kingdom .

OTHER PUBLICATIONS

"Selective Olefin Epoxidation at High Hydroperoxide-to-Olefin Ratios", J. Catal. 43, (1976), pp. 380 to 383.

Primary Examiner—Frederick E. Waddell
Assistant Examiner—Ba K. Trinh
Attorney, Agent, or Firm—Fisher, Christen & Sabol

[57] ABSTRACT

A novel method for preparing an epoxy compound is disclosed which comprises the step of reacting an olefin compound having 4 to 16 carbon atoms with an organic hydroperoxide in an inactive solvent in the presence of a molybdenum compound and at least one metal halide selected from the group consisting of halides of alkali metals and alkaline earth metals, in order to form the corresponding epoxy compound. Typical examples of the aforesaid metal halide include sodium chloride, potassium iodide, sodium bromide and barium chloride. According to the present invention, the epoxy compound having 4 to 16 carbon atoms can be prepared in an extremely high yield.

18 Claims, No Drawings

METHOD FOR PREPARING EPOXY COMPOUND

BACKGROUND OF THE INVENTION (1) Field of the Invention

The present invention relates to a method for preparing an epoxy compound in a high yield by oxidizing an olefin compound having 4 to 16 carbon atoms with an organic hydroperoxide.

(2) Description of the Prior Art

Epoxy compounds are very reactive and important compounds which can be converted into polyethers, glycols and other kinds of chemicals by reactions with various compounds.

Heretofore, these epoxy compounds have been manufactured by forming a corresponding halohydrin from an olefin compound having a corresponding carbon skeleton, and then subjecting the halohydrin to a dehydrogenation reaction by the use of a basic compound such as calcium hydroxide. Further, as another method of oxidation, an epoxidation technique is also known which utilizes an organic peracid such as performic acid, peracetic acid or perbenzoic acid.

Still another method for manufacturing epoxy compounds has been extensively researched which comprises the epoxidation reaction of an olefin compound where an organic hydroperoxide is used as the oxidizing agent. In this epoxidation reaction, a catalyst is used which is an organic metallic compound of a metal selected from the group consisting of molybdenum, tungsten and vanadium.

In order to improve the selectivity of the desired epoxidation reaction, various methods are known in which a second substance is used together with a conventional known epoxidation catalyst in the epoxidation reaction of the olefin with the organic hydroperoxide. For example, J. Catal., 43, 380-383 (1976) describes that, in oxidizing 1-octene with cumene hydroperoxide in the presence of a molybdenum naphthenate catalyst to form 1-octene oxide, an oxide of an alkaline earth metal such as barium oxide, strontium oxide, calcium oxide or magnesium oxide is used simultaneously so as to remarkably heighten the selectivity of the epoxidation. Further, Japanese Patent Laid-open No. 133279/1981 discloses a method for epoxidizing an olefin compound having 4 carbon atoms with an organic hydroperoxide in which the reaction occurs in the presence of an organic amine compound and an organic metallic compound of a metal selected from the group consisting of molybdenum, vanadium and tungsten.

The halohydrin method which is a typical example of the above-mentioned conventional technique, has the disadvantages that the halogen for example, chlorine, consumed by the halohydrin is completely converted into its less valuable inorganic salt, i.e., calcium chloride, and a dilute aqueous solution containing this inorganic salt is byproduced in large quantities. Therefore, for the purpose of finding oxidizing methods in which no halogen is used, research has been made into an oxidizing method using an organic peracid and into a catalytic epoxidation method using an organic hydroperoxide as the oxidizing agent.

However, in an epoxidation reaction with an organic peracid, the ring-opening-addition reaction of the produced epoxide with a byproduced acid cannot be avoided, with the result that the epoxy compound cannot be obtained in a high yield.

Further, for example, in the aforesaid catalytic reaction of using an organic hydroperoxide, an olefin compound can be epoxidized in the presence of an organic compound of molybdenum as the catalyst, but there is the problem that the selectivity is not always high. Accordingly, there is a need to establish a method for preparing an epoxy compound with a high selectivity.

SUMMARY OF THE INVENTION

With the intention of solving the above-mentioned problems, the inventors of the present application conducted extensive research into the epoxidation reaction of olefin compounds having 4 to 16 carbon atoms with organic hydroperoxides. As a result, they found that, when a reaction is carried out in the presence of a molybdenum compound as a catalyst and a halide of an alkali metal or a halide of an alkaline earth metal, the desired epoxy compound can be produced in a high yield of not less than 90% or in a substantially quantitative yield in certain cases. The present invention has been achieved on the basis of this finding.

According to the present invention, epoxy compounds having 4 to 16 carbon atoms can be very easily prepared in a remarkably high selectivity which is close to the theoretical level, in contrast to conventional known epoxidation methods. The selectivity here referred to is calculated on the basis of an organic hydroperoxide or a raw material olefin compound having 4 to 16 carbon atoms. In the present invention, the selectivity of the epoxidation for the raw material olefin can be increased significantly, and therefore it is fair to say that the present invention is very beneficial industrially as a method for manufacturing an epoxy compound having 4 to 16 carbon atoms by the use of an organic hydroperoxide.

DETAILED DESCRIPTION OF THE INVENTION

The present invention is directed to a method for preparing an epoxy compound which comprises the step of reacting an olefin compound having 4 to 16 carbon atoms with an organic hydroperoxide in an inactive solvent in the presence of a molybdenum compound and at least one metal halide selected from the group consisting of halides of alkali metals and alkaline earth metals to form the corresponding epoxy compound.

Examples of the olefin compounds having 4 to 16 carbon atoms used in the present invention include butenes such as isobutylene, trans- and cis-2-butenes, 1-butene; pentenes such as 1-pentene, trans- and cis-2-pentenes and 2-methyl-1-butene; hexenes such as 1-hexene, trans- and cis-2-hexenes, trans- and cis-3-hexenes, 2,3-dimethyl-1-butene, 2-methyl-1-pentene and cyclohexene; and straight-chain, branched and cyclic aliphatic olefin hydrocarbons each having 16 or less carbon atoms.

The preferable molybdenum compound used as the catalyst in the present invention is an organic metallic compound which is soluble in a reaction system and which can be obtained from an oxide of molybdenum such as molybdenum oxide acetylacetonate or molybdenum naphthenate.

In the present invention, typical halides of the alkali metals are the halides of lithium, sodium, potassium, rubidium and cesium, and typical halides of the alkaline earth metals are the halides of beryllium, magnesium, calcium, strontium and barium. Examples of the halogen include chlorine, bromine and iodine, and the halides of these halogens may be used singly or in a combination of two or more thereof. In particular, sodium chloride is preferred.

When the above-mentioned metal halide is used together with the molybdenum catalyst, the selectivity in the epoxidation can be improved remarkably. With regard to the amount of the metal halide, its lower limit is about 0.0001% by weight in the reaction solution, depending on the kind of olefin compound which is involved in the reaction, the kind of organic hydroperoxide which is the oxidizing agent, and reaction conditions such as reaction temperatures and concentrations of the materials. The trace addition of the metal halide can provide a perceptible effect. The upper limit of the amount of the metal halide is not particularly limited, but it is about 5% by weight in the reaction liquid. When the metal halide is added in excess of the upper limit, a concentrated slurry is formed, so that operation becomes difficult, and the addition efficiency of the metal halide deteriorates.

In the present invention, any kind of organic hydroperoxides which are epoxidizing agents can be used, but examples of effective organic hydroperoxides which are readily available industrially include ethylbenzene hydroperoxide, cumene hydroperoxide and tert-butyl hydroperoxide.

The ratio of the organic hydroperoxide to the olefin compound can optionally be selected. However, when unreacted hydroperoxide remains after the epoxidation reaction, the separation of the unreacted hydroperoxide is necessary in the recovery and purification steps, and safety is also impaired. Therefore, it is preferred that the reaction be performed with an excessive amount of the olefin compound so as to increase the conversion of the hydroperoxide as much as possible. In other words, the molar ratio of the olefin compound to the organic hydroperoxide is suitably from 1 to 15. If the molar ratio of the olefin compound is too high, a large amount of the unreacted olefin compound must be recovered. For this reason, it is preferable not to use the olefin compound in a molar ratio higher than 15.

In the epoxidation reaction, an inactive solvent can be used. Examples of the inactive solvent used in the reaction include aliphatic hydrocarbons each having 1 to 10 carbon atoms, aromatic hydrocarbons and halogenated hydrocarbons in which the raw material olefin and the organic hydroperoxide can be dissolved. However, in order to simplify separation and recovery after the reaction, it is preferable to use the same kind of material as the precursor of the organic hydroperoxide, the precursor being contained in the organic hydroperoxide. For example, in the case that cumene hydroperoxide is employed, cumene is preferably used, and in the case that ethylbenzene hydroperoxide is employed, ethylbenzene is preferably used. In general, the organic hydroperoxide is used at a concentration of 5 to 90% by weight in its precursor.

The reaction temperature is in the range of 50° to 150° C., preferably 70° to 110° C., and the reaction time is in the range of about 10 minutes to about 10 hours. Other reaction conditions can be optionally decided in accordance with the kind of organic hydroperoxide, the kind of olefin compound corresponding to the desired epoxy compound, and other factors.

The reaction can be performed in a continuous type stirring tank or a batch type stirring tank. The above-mentioned metal halide can be easily separated from the resulting synthetic reaction solution by means of filtration or standing/sedimentation. Afterward, the raw material olefin can be recovered from the remaining solution by distillation, and the desired epoxy compound can be then recovered by distillation under reduced pressure.

In conventional techniques, the following can be assumed. As discussed in the "Description of the Prior Art" above, for example in the case that an oxide of an alkaline earth metal is added or in the case that an organic amine compound is added, the basic compound is added to prevent the reaction system from becoming acidic, or to neutralize an acidic substance in the reaction system, with the result that the undesirable acid decomposition of the organic hydroperoxide is inhibited.

The important and surprising feature of the present invention is that the yield of the product on the basis of the organic hydroperoxide or particularly the raw material olefin can be improved very effectively by using a quite neutral salt which is different from conventional basic compounds. Further, the above-mentioned metal halide is substantially insoluble or only barely soluble in the reaction system under the reaction conditions of the present invention, and thus it can be easily separated by filtration or standing/sedimentation after the completion of the reaction. Additionally, the present invention has neither the problem that the metal halide is brought into the recovery step of the epoxy compound, so that an additional reaction occurs and the desired epoxy compound is lost, nor the problem that the epoxy compound is contaminated with the metal halide as an impurity.

The present invention will be described in detail by reference to examples.

Here, the selectivity of the epoxy compound (hereinafter referred to simply as "oxide") on the basis of the raw material olefin compound (hereinafter referred to simply as "olefin") having 4 to 16 carbon atoms and the selectivity of the oxide on the basis of the organic hydroperoxide (hereinafter referred to simply as "HPO") were each obtained by the following procedure:

(1) The selectivity (%) of the oxide on the basis of the olefin $= [D/(E-F)] \times 100$ D = moles of the oxide produced by the reaction,
E = moles of the oxide fed to the reaction system, and
F = moles of the remaining olefin after the reaction.

(2) The selectivity (%) of the oxide on the basis of HPO $= [A/(B-C)] \times 100$ A = moles of the oxide produced by the reaction,
B = moles of the HPO fed to the reaction system, and
C = moles of the remaining HOP after the reaction.

EXAMPLE 1

In a 300-milliliter stainless steel autoclave were placed 40 g of cumene and 0.03 g of molybdenum oxide acetyl acetate (hereinafter referred to as "MoAcAc") and 0.09 g of sodium chloride, and the autoclave was then covered with a lid. Afterward, 11.3 g (0.202 mole) of isobutylene (hereinafter referred to as "I-BU") was added thereto through a pressure-resistant holder. The temperature of the solution was then raised to 95° C. under agitation, and 85.1 g of a cumene solution (0.103 mole as HPO) containing 30% by weight of cumene hydroperoxide was fed to the autoclave over about 30 minutes by means of a pump. Afterward, the solution was further agitated for 1 hour at the same temperature, and the temperature of the solution was then lowered.

The resulting reaction solution was analyzed by gas chromatography, and a chemical analysis method was used for HPO. As a result, the conversion of I-BU was 42.2%, the selectivity of isobutylene oxide (hereinafter referred to as "I-BO") on the basis of I-BU was 96.3%, the conversion of HPO was 95.4%, the selectivity of I-BO on the basis of HPO was 83.5%, and particularly on the basis of the olefin, the reaction result of I-BO was good, i.e., substantially quantitative.

EXAMPLE 2

Reaction and analysis were performed following the same procedure as in Example 1, except that 11.3 g (0.202 mole) of 2-butene (hereinafter referred to as "2-BU") was used in place of I-BU. As a result, the conversion of 2-BU was 43.2%, the selectivity of 2-butene oxide (hereinafter referred to as "2-BO") on the basis of 2-BU was 95.8%, the conversion of HPO was 96.6%, and the selectivity of 2-BO on the basis of HPO was 84.1%.

EXAMPLE 3

Reaction and analysis were performed following the same procedure as in Example 1, except that 0.1 g of barium chloride was used in place of sodium chloride. As a result, the conversion of I-BU was 42.5%, the selectivity of I-BO on the basis of I-BU was 96.1%, the conversion of HPO was 95.8%, and the selectivity of I-BO on the basis of HPO was 83.7%.

EXAMPLE 4

In the same autoclave as in Example 1 were placed 63.0 g of cumene, 0.03 g of MoAcAc and 0.1 g of potassium iodide, and the autoclave was then covered with a lid. Afterward, 14.7 g (0.262 mole) of I-BU was added thereto through a pressure-resistant holder. The temperature of the solution was then raised to 95° C. under agitation, and 55.7 g of a cumene solution (0.22 mole as HPO) containing 60% by weight of cumene hydroperoxide was fed to the autoclave over about 30 minutes by means of a pump. Afterward, the solution was further agitated for 1 hour at the same temperature, and the temperature of the solution was then lowered. As the result of a similar analysis, the conversion of I-BU was 71.5%, the selectivity of I-BO on the basis of I-BU was 95.7%, the conversion of HPO was 97.0%, and the selectivity of I-BO on the basis of HPO was 84.0%.

EXAMPLE 5

Reaction and analysis were performed following the same procedure as in Example 4, except that 0.1 g of sodium bromide was used in place of potassium iodide. As a result, the conversion of I-BU was 68.4%, the selectivity of I-BO on the basis of I-BU was 96.2%, the conversion of HPO was 96.9%, and the selectivity of I-BO on the basis of HPO was 84.1%.

EXAMPLE 6

Reaction and analysis were performed following the same procedure as in Example 4, except that MoAcAc was replaced with 0.03 g of molybdenum naphthenate and potassium iodide was replaced with 0.09 g of NaCl. As a result, the conversion of I BU was 70.5%, the selectivity of I-BO on the basis of I-BU was 96.2%, the conversion of HPO was 96.2%, and the selectivity of I-BO on the basis of HPO was 83.9%.

EXAMPLE 7

Reaction was performed following the same procedure as in Example 1, except that in place of I-BU, 43.3 g (0.515 mole) of 1-hexene (hereinafter referred to as "1-Hex") was dissolved in 80 g of cumene, and after the feed of HPO had been over, the solution was further agitated for 4 hours, and the temperature of the solution was then lowered. The resulting reaction solution was analyzed in the same manner as in Example 1. As a result, the conversion of 1-Hex was 16.1%, the selectivity of hexene oxide (hereinafter referred to as "HO") on the basis of 1-Hex was 95.7%, the conversion of HPO was 95.5%, and the selectivity of HO on the basis of HPO was 80.9%.

EXAMPLE 8

Reaction and analysis were performed following the same procedure as in Example 7, except that in place of 1-hexene, 40.5 g (0.361 mole) of 1-octene (hereinafter referred to as "1-Oct") was dissolved in 80 g of cumene and that 42.6 g of a cumene solution (0.052 mole as HPO) containing 30% by weight of cumene hydroperoxide was fed thereto. As a result, the conversion of I-Oct was 11.9%, the selectivity of octene oxide (hereinafter referred to as "OO") on the basis of I-Oct was 94.4%, the conversion of HPO was 95.5%, and the selectivity of OO on the basis of HPO was 82.2%.

COMPARATIVE EXAMPLE 1

Reaction and analysis were performed following the same procedure as in Example 1, except that no sodium chloride was added. As a result, the conversion of I-BU was 46.6%, the selectivity of I-BO on the basis of I-BU was 81.7%, the conversion of HPO was 94.1%, and the selectivity of I-BO on the basis of HPO was 78.1%.

COMPARATIVE EXAMPLE 2

Reaction and analysis were performed following the same procedure as in Example 1, except that sodium chloride was replaced with calcium oxide. As a result, the conversion of I-BU was 47.4%, the selectivity of I-BO on the basis of I-BU was 82.5%, the conversion of HPO was 95.4%, and the selectivity of I-BO on the basis of HPO was 80.3%.

COMPARATIVE EXAMPLE 3

In the same autoclave as in Example 1 were placed 40 g of cumene, 0.2 g of molybdenum naphthenate and 0.01 g of ammonium chloride, and the autoclave was then covered with a lid. Afterward, 11.3 g (0.202 mole) of I-BU was added thereto through a pressure-resistant holder. The temperature of the solution was then raised to 95° C. under agitation, and 85.1 g of a cumene solution (0.103 mole as HPO) containing 30% by weight of cumene hydroperoxide was fed to the autoclave over about 30 minutes by means of a pump. Afterward, the solution was further agitated for 1 hour at the same temperature, and the temperature was then lowered. The resulting reaction solution was analyzed by gas chromatography, a chemical analysis method was used for HPO. As a result, the conversion of I-BU was 50.5%, the selectivity of I-BO on the basis of I-BU was 74.2%, the conversion of HPO was 91.4%, and the selectivity of I-BO on the basis of HPO was 80.4%.

What is claimed is:

1. A method for preparing an epoxy compound which comprises the step of reacting an olefin compound having 4 to 16 carbon atoms with an organic hydroperoxide in an inactive solvent in the presence of a molybdenum compound and at least one metal halide selected from the group consisting of halides of alkali metals and alkaline earth metals, to form said corresponding epoxy compound.

2. A method for preparing an epoxy compound according to claim 1 wherein said olefin compound has 4 to 10 carbon atoms.

3. A method for preparing an epoxy compound according to claim 1 wherein said halide of the alkali metal is sodium chloride.

4. A method for preparing an epoxy compound according to claim 1 wherein said halide of the alkali metal is potassium iodide.

5. A method for preparing an epoxy compound according to claim 1 wherein said halide of the alkali metal is sodium bromide.

6. A method for preparing an epoxy compound according to claim 1 wherein said halide of the alkaline earth metal is barium chloride.

7. A method for preparing an epoxy compound according to claim 1 wherein said molybdenum compound is an oxide of molybdenum.

8. A method for preparing an epoxy compound according to claim 7 wherein said oxide of molybdenum is molybdenum oxide acetylacetonate.

9. A method for preparing an epoxy compound according to claim 7 wherein said oxide of molybdenum is molybdenum naphthenate.

10. A method for preparing an epoxy compound according to claim 1 wherein said olefin compound is isobutylene.

11. A method for preparing an epoxy compound according to claim 1 wherein said olefin compound is 1-butene.

12. A method for preparing an epoxy compound according to claim 1 wherein said olefin compound is 2-butene.

13. A method for preparing an epoxy compound according to claim 1 wherein said olefin compound is 1-hexene.

14. A method for preparing an epoxy compound according to claim 1 wherein said olefin compound is 1-octene.

15. A method for preparing an epoxy compound according to claim 1 wherein said organic hydroperoxide is cumene hydroperoxide.

16. A method for preparing an epoxy compound according to claim 1 wherein said inactive solvent is cumene.

17. A method for preparing an epoxy compound according to claim 1 wherein said reaction is carried out at a temperature of 50° to 150° C.

18. A method for preparing an epoxy compound which further involves the step of recovering said epoxy compound in claim 1.

* * * * *